United States Patent
Hollister et al.

(10) Patent No.: US 12,303,404 B2
(45) Date of Patent: May 20, 2025

(54) GRAFT DELIVERY SYSTEM

(71) Applicant: Spine Wave, Inc., Shelton, CT (US)

(72) Inventors: Ty Hollister, Shelton, CT (US);
Hughues Malandain, Easton, CT (US);
Peter Barreiro, West Haven, CT (US);
Claire Battista, Wolcott, CT (US)

(73) Assignee: Spine Wave, Inc., Shelton, CT (US)

( * ) Notice: Subject to any disclaimer, the term of this patent is extended or adjusted under 35 U.S.C. 154(b) by 0 days.

(21) Appl. No.: 18/609,389

(22) Filed: Mar. 19, 2024

(65) Prior Publication Data

US 2024/0216149 A1 Jul. 4, 2024

Related U.S. Application Data

(60) Continuation of application No. 17/544,321, filed on Dec. 7, 2021, now Pat. No. 11,944,554, which is a continuation of application No. 16/691,834, filed on Nov. 22, 2019, now Pat. No. 11,207,194, which is a division of application No. 15/447,702, filed on Mar. 2, 2017, now Pat. No. 10,492,925.

(60) Provisional application No. 62/303,059, filed on Mar. 3, 2016.

(51) Int. Cl.
| | |
|---|---|
| *A61F 2/46* | (2006.01) |
| *A61F 2/28* | (2006.01) |
| *A61F 2/44* | (2006.01) |

(52) U.S. Cl.
CPC .......... *A61F 2/4601* (2013.01); *A61F 2/4455* (2013.01); *A61F 2002/2835* (2013.01); *A61F 2/4603* (2013.01); *A61F 2002/4627* (2013.01)

(58) Field of Classification Search
CPC ..................................................... A61F 2/4601
See application file for complete search history.

(56) References Cited

U.S. PATENT DOCUMENTS

| | | | |
|---|---|---|---|
| 4,451,254 A | 5/1984 | Dinius et al. | |
| 4,533,019 A | 8/1985 | Leding | |
| 4,800,875 A | 1/1989 | Ray | |
| 5,925,051 A | 7/1999 | Mikhail | |
| 6,059,829 A | 5/2000 | Schlapfer et al. | |
| 6,248,110 B1* | 6/2001 | Reiley | A61B 17/8805 |
| | | | 606/92 |
| 6,616,593 B1 | 9/2003 | Elliott et al. | |
| 8,308,805 B2 | 11/2012 | Lynn et al. | |
| 8,425,612 B2 | 4/2013 | Perez-Cruet et al. | |

(Continued)

*Primary Examiner* — Christian A Sevilla
(74) *Attorney, Agent, or Firm* — Hoffmann & Baron, LLP

(57) ABSTRACT

A system for delivering bone graft material into an interbody fusion device (IBFD) in an intradiscal space of a spine, the IBFD having an open-frame with a hollow interior and an opening through its proximal end communicating with the interior. Included is an elongate channel having a lumen extending therethrough, the distal end being in engagement with the IBFD to align the lumen with the opening through the proximal end of the IBFD. An adjustable block is movably attached to the channel, the block having plural chambers containing bone graft material, the chambers being individually sequentially alignable with the lumen. A plunger pushes graft material from each chamber, through the lumen and into the IBFD. A distal end of a tamper is configured to be inserted through each chamber and the lumen and into the IBFD interior for tamping graft material deposited into the interior of the IBFD.

8 Claims, 14 Drawing Sheets

(56) References Cited

U.S. PATENT DOCUMENTS

| | | |
|---|---|---|
| 8,641,769 B2 | 2/2014 | Malandain |
| 8,740,908 B2 | 6/2014 | Farley et al. |
| 8,852,282 B2 | 10/2014 | Farley et al. |
| 9,101,489 B2 | 8/2015 | Protopsaltis et al. |
| 9,393,057 B2 | 7/2016 | MacMillan et al. |
| 11,559,342 B2* | 1/2023 | Ju ................... A61B 17/8822 |
| 2004/0098017 A1* | 5/2004 | Saab .................. A61B 17/8855 |
| | | 606/192 |
| 2007/0043376 A1 | 2/2007 | Leatherbury et al. |
| 2007/0225809 A1 | 9/2007 | Ray |
| 2008/0125856 A1 | 5/2008 | Perez-Cruet et al. |
| 2008/0172128 A1 | 7/2008 | Perez-Cruet et al. |
| 2011/0319995 A1* | 12/2011 | Voellmicke ............ A61F 2/447 |
| | | 623/17.11 |
| 2013/0006365 A1 | 1/2013 | Pepper et al. |
| 2013/0006366 A1 | 1/2013 | Farley et al. |
| 2013/0345710 A1* | 12/2013 | Kleiner .................... A61F 2/44 |
| | | 606/94 |
| 2016/0106551 A1* | 4/2016 | Grimberg, Jr. ........ A61F 2/4601 |
| | | 623/17.16 |
| 2016/0228261 A1 | 8/2016 | Emery et al. |

\* cited by examiner

IBFD
36

GRAFT DELIVERY SYSTEM

CROSS-REFERENCES TO RELATED APPLICATIONS

This application is a continuation application of U.S. patent application Ser. No. 17/544,321, Filed Dec. 7, 2021, now, now U.S. Pat. No. 11,944,554, which is a continuation of U.S. patent application Ser. No. 16/691,834, filed Nov. 22, 2019, now U.S. Pat. No. 11,207,194, which is a divisional application of U.S. application Ser. No. 15/447,702, filed Mar. 2, 2017, now U.S. Pat. No. 10,492,925, which claims the benefit of U.S. Provisional Patent Application No. 62/303,059, filed Mar. 3, 2016, the entire contents of which are incorporated by reference herein.

BACKGROUND OF THE INVENTION

Interbody fusion devices are well known in the prior art, including expandable interbody fusion devices and fixed-height interbody fusion devices. Examples of expandable interbody fusion devices may be found in U.S. Pat. Nos. 8,641,769 and 9,101,489, both to the assignee herein, and both which are incorporated by reference herein. Further examples of interbody fusion devices, both expandable and fixed-height, are found in devices sold by Spine Wave, Inc., of Shelton, Connecticut, U.S.A., under the brand name "LEVA".

As is well known with techniques relating to implantation of interbody fusion devices, graft material is typically introduced in and about an implanted device to foster bone fusion between target vertebrae. Various techniques are known in the prior art for introducing graft material intradiscally. Typically, a column is packed with graft material along its full length and introduced into the intradiscal space. Graft material is urged from the column as needed. Often, the full amount of graft material packed into the column is not utilized, leading to wasteful disposal.

SUMMARY OF THE INVENTION

A system is provided herein for delivering graft material into an intradiscal space, particularly after implantation of an interbody fusion device. The system, in a broadest aspect, generally includes a channel with which is associated a multi-chambered adjustable block. Individual chambers of the block may be each loaded with an amount of graft material which can be sequentially introduced through the channel to a target site utilizing a plunger. In this manner, graft material in unused chambers may be salvaged. In addition, with the use of multiple chambers, different types of graft material may be packed into different chambers so as to allow for combinations of graft material to be located at the target site.

In a further aspect of the subject invention, one or more tampers may be provided for tamping graft material discharged from the channel. A set of the tampers may be provided, with each of the tampers having a different-sized paddle extending from the distal end thereof which allows for different levels of tamping and adjusting of graft materials in situ.

DETAILED DESCRIPTION

Figure 1:
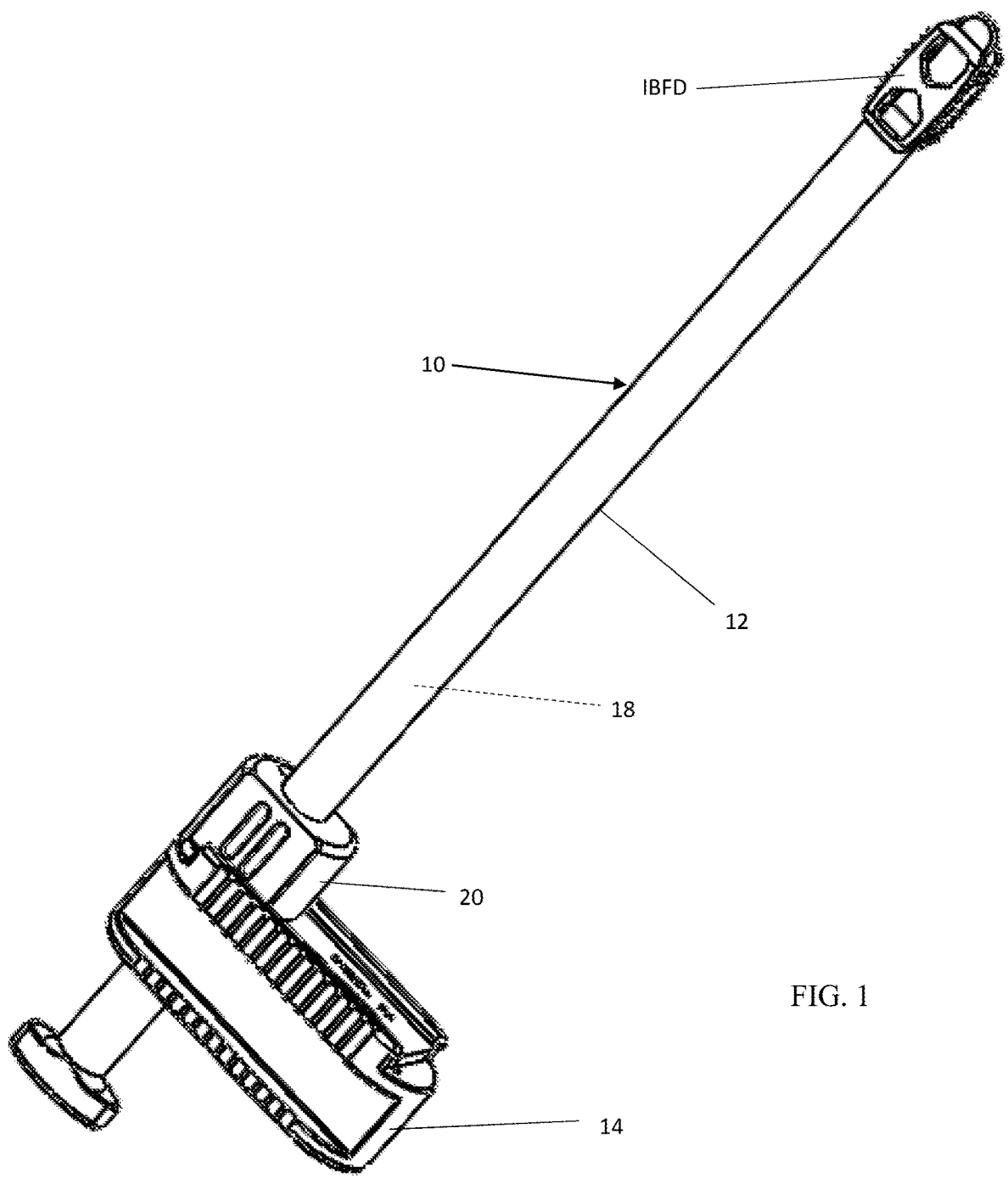
FIG. 1 is a perspective view of the bone graft delivery system in accordance with one particular arrangement of the invention.

With reference to the attached Figures, a system 10 is provided for delivering graft material into an intradiscal space, particularly after implantation of an interbody fusion device (IBFD). The system 10 may be utilized with various interbody fusion devices, including expandable interbody fusion devices and fixed-height interbody fusion devices, including, but not limited to, devices sold by Spine Wave, Inc. under the brand name "LEVA" and devices found in U.S. Pat. Nos. 8,641,769 and 9,101,489, which are incorporated by reference herein.

The system 10 includes a channel 12 with which is associated a multi-chambered adjustable block 14. The block 14 includes a plurality of chambers 16 formed to accommodate graft material.

The block 14 may be formed to be adjustable relative to the channel 12 in various manners. Sequential introduction of the chambers 16 in alignment with a lumen 18 of the channel 12 is desired. By way of non-limiting example, the Figures herein show an axially adjustable arrangement, whereby the block 14 may be adjusted transversely relative to the lumen 18. Other adjustments may be possible, including rotation of the block 14 about an axis transverse to the lumen 18, e.g., with the chambers 16 being formed to radiate outwardly in the block 14, or rotation of the block 14 about an axis parallel to the lumen 18.

Figure 2:
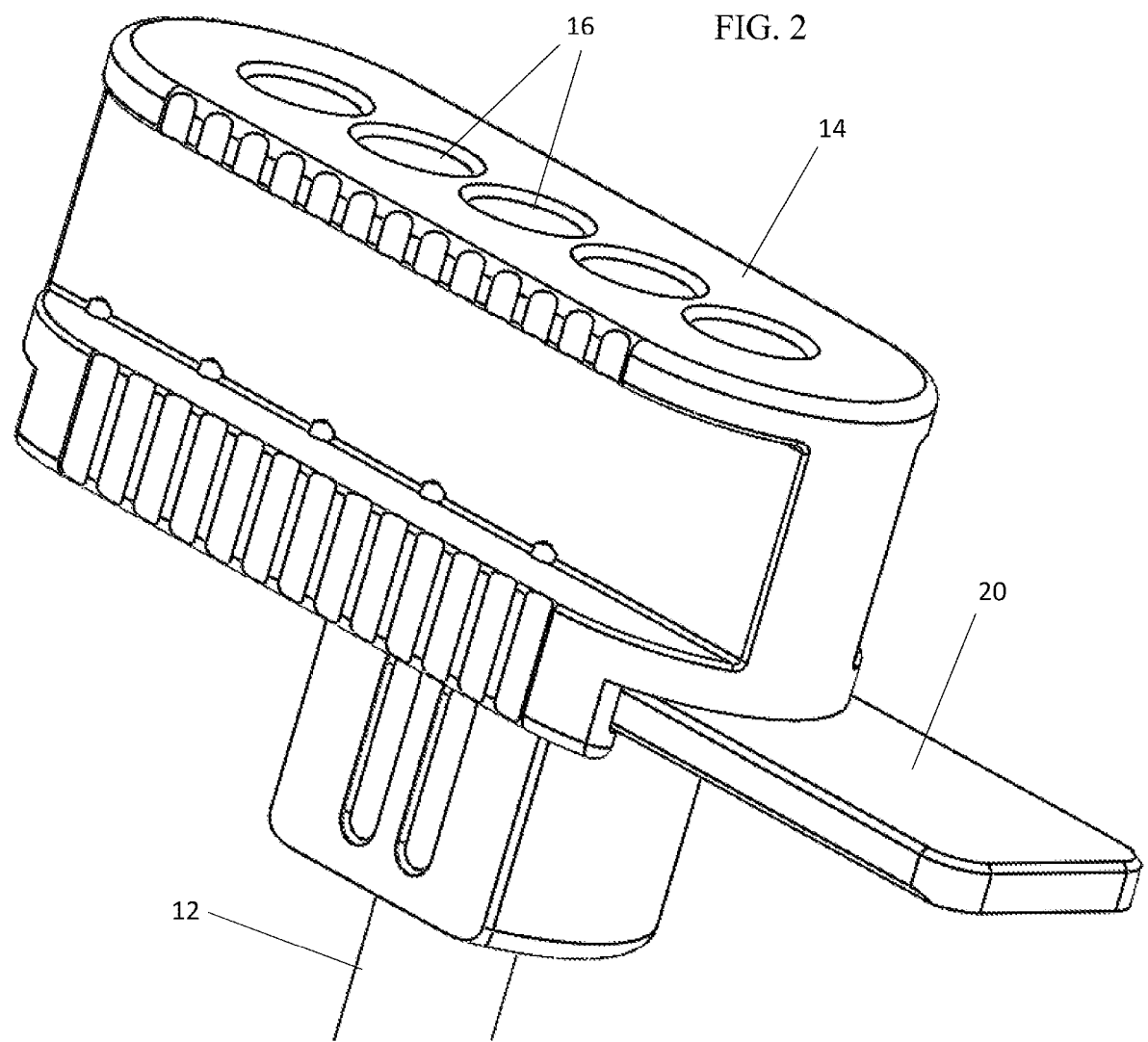
FIG. 2 is an enlarged perspective view of the proximal end of a bone graft delivery apparatus used in the system of FIG. 1.
Figure 3:
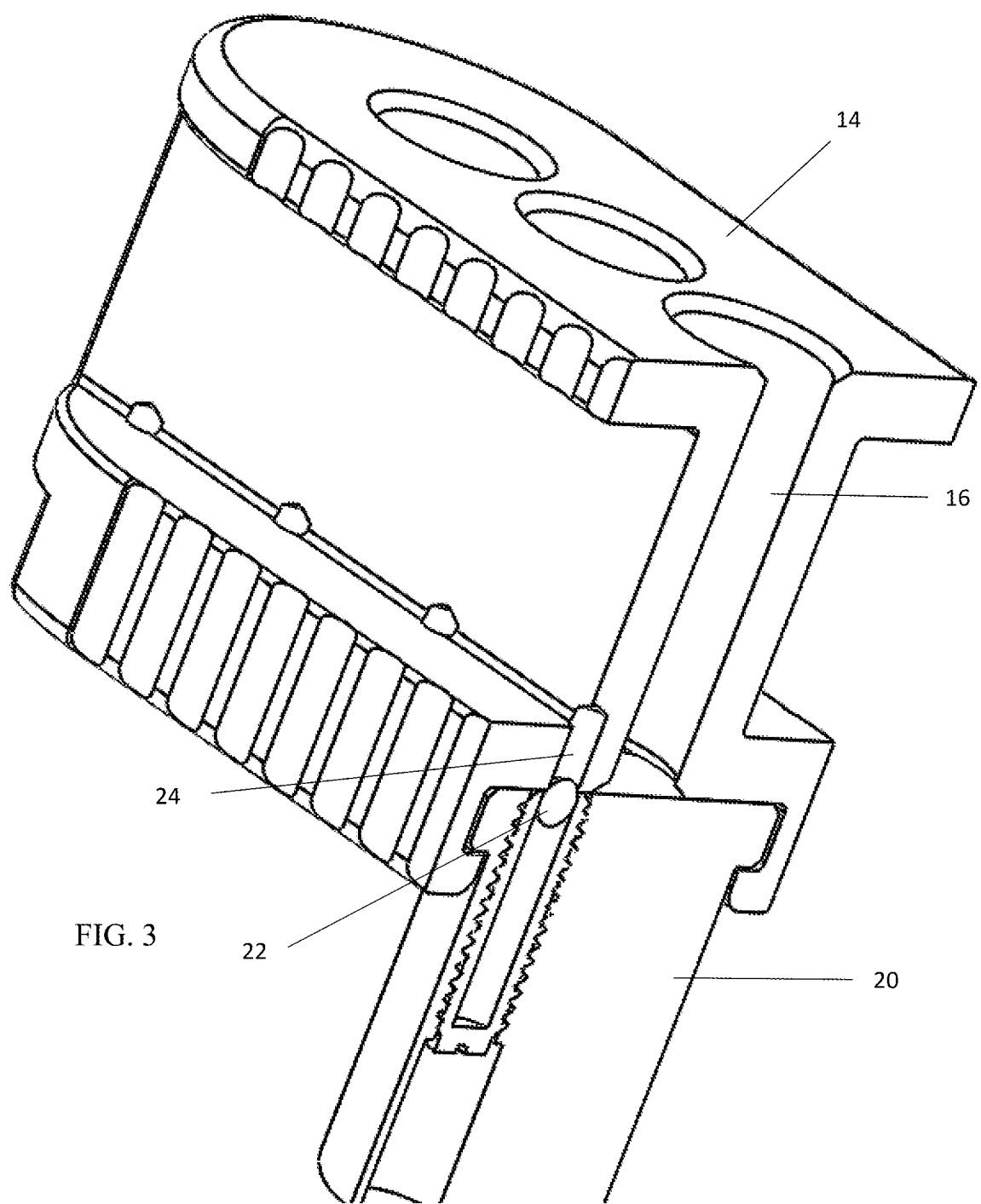
FIG. 3 is a perspective longitudinal section of the proximal end of the bone graft delivery apparatus of FIG. 2 showing details of a particular arrangement of a releasable locking mechanism.

With reference to the FIGS. 1-2, a bracket 20 may be secured at or in proximity to a proximal end of the channel 12, leaving open the lumen 18. The block 14 is configured to be slideably mounted to the bracket 20 to allow for sequential alignment of the chambers 16 with adjustment of the block 14 relative to the lumen 18. Optionally, a releasable locking mechanism may be provided which provides a retaining force for maintaining the block 14 in a fixed position relative to the bracket 20. Various resilient and surmountable arrangements may be provided which require a threshold amount of force to be overcome to achieve adjustment. With reference to FIG. 3, a spring-biased locking member 22 may be provided on one of the block 14 or the bracket 20 with corresponding locking apertures 24 being formed in the other of the block 14 and the bracket 20.

The locking apertures 24 are formed so that the locking member 22 may be seated therein to resist adjustment of the block 14 relative to the bracket 20. The locking apertures 24 are positioned to correspond to positions of the block 14 relative to the channel 12, more particularly, positions which allow for alignment of the chambers 16 relative to the lumen 18. With sufficient manual force being applied, the locking member 22 is displaced to permit adjustment of the block 14 relative to the bracket 20. Preferably, the locking member 22 is located on the block 14. It is envisioned that during use, the block 14 will be a disposable single-use component with the channel 12 being re-used with sterilization. With the locking member 22 located on the block 14, the locking member 22 will be disposed with the block 14 avoiding the need for sterilization thereof. With this arrangement, the locking apertures 24 would be sterilized with the channel 12.

Optionally, the system 10 may be provided as a disposable single-use component. In addition, or, alternatively, the channel 12 may be formed to be detached from the block 14 to allow for disposal of either component with re-use of the other component.

Figure 9:
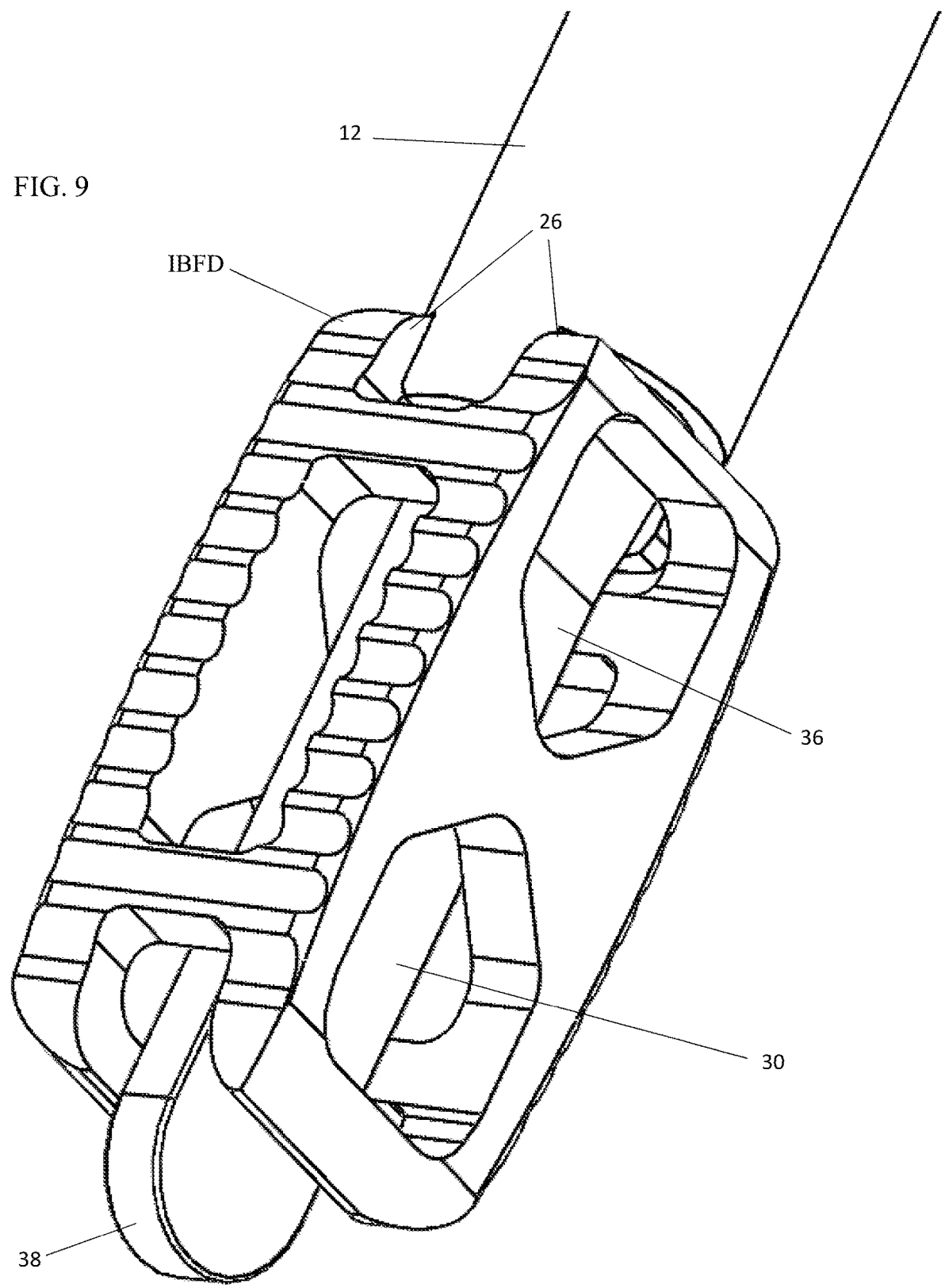
FIGS. 9 and 10 are enlarged perspective views of the distal end of the bone graft delivery system of FIG. 1 showing the distal end of a tamper paddle situated within the interior of an open framed interbody fusion device.
Figure 10:
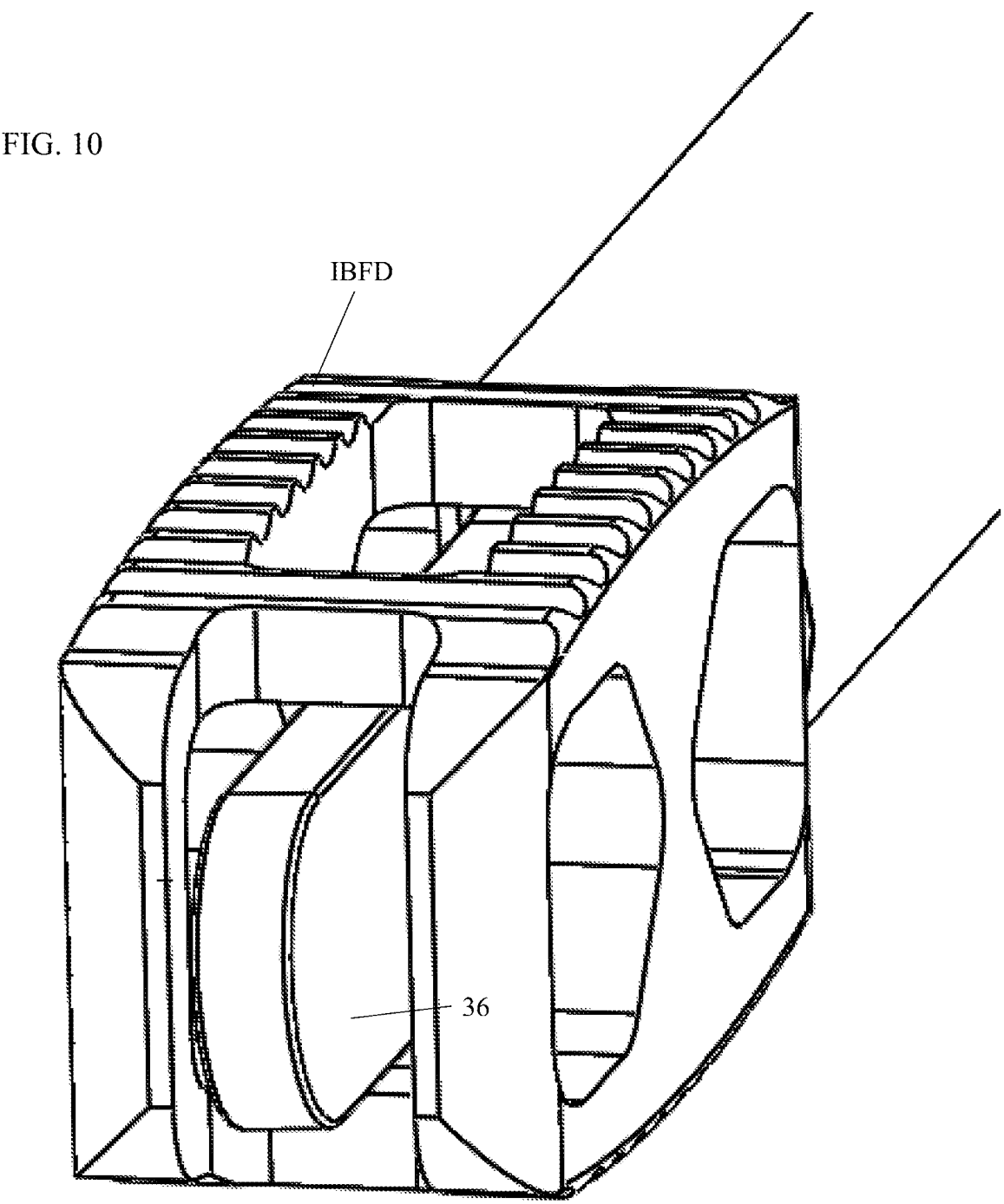

With reference to FIG. 1, the system 10 is introduced during a procedure once an interbody fusion device (IBFD) has been implanted. The system 10 may be introduced through a cannula, dilator or other structure defining a passageway to the target site. Preferably, the distal end of the channel 12 is formed with features 26 configured to engage the interbody fusion device to allow for alignment therewith. As shown in FIG. 9, the features 26 may include cut-outs formed to seatingly receive portions of the interbody fusion device. Preferably, the lumen 18 is aligned to discharge graft material into an interior of the interbody fusion device. The system 10 is particularly well-suited for use with open-frame interbody fusion devices such as that shown in FIG. 9.

The chambers 16 are prepared for procedure with placement of graft material therein. The graft material may be pre-packaged in the chambers 16 and/or packaged on site. The graft material may be of any known type, including, but not limited to, autograft, allograft, and xenograft (both animal and human) graft material. The graft material may be varied both within the chambers 16 and between the chambers 16.

Figure 4:
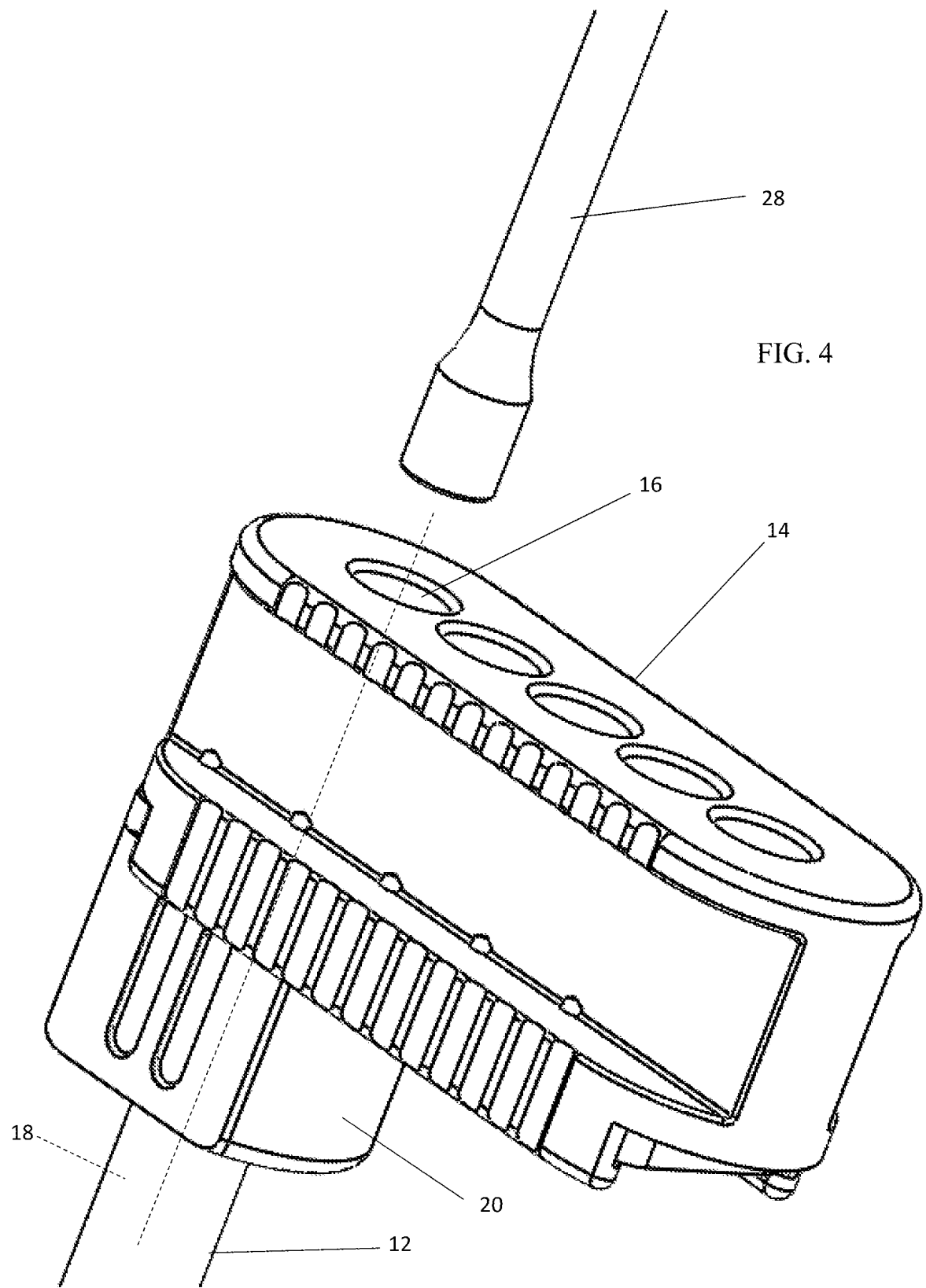
FIGS. 4-8 are perspective successive views of the proximal end of the bone graft delivery apparatus of FIG. 2 showing the incremental movement of the adjustable block with sequential alignment of each of the plurality of adjustable block chambers relative to the channel of the delivery apparatus.
Figure 5:
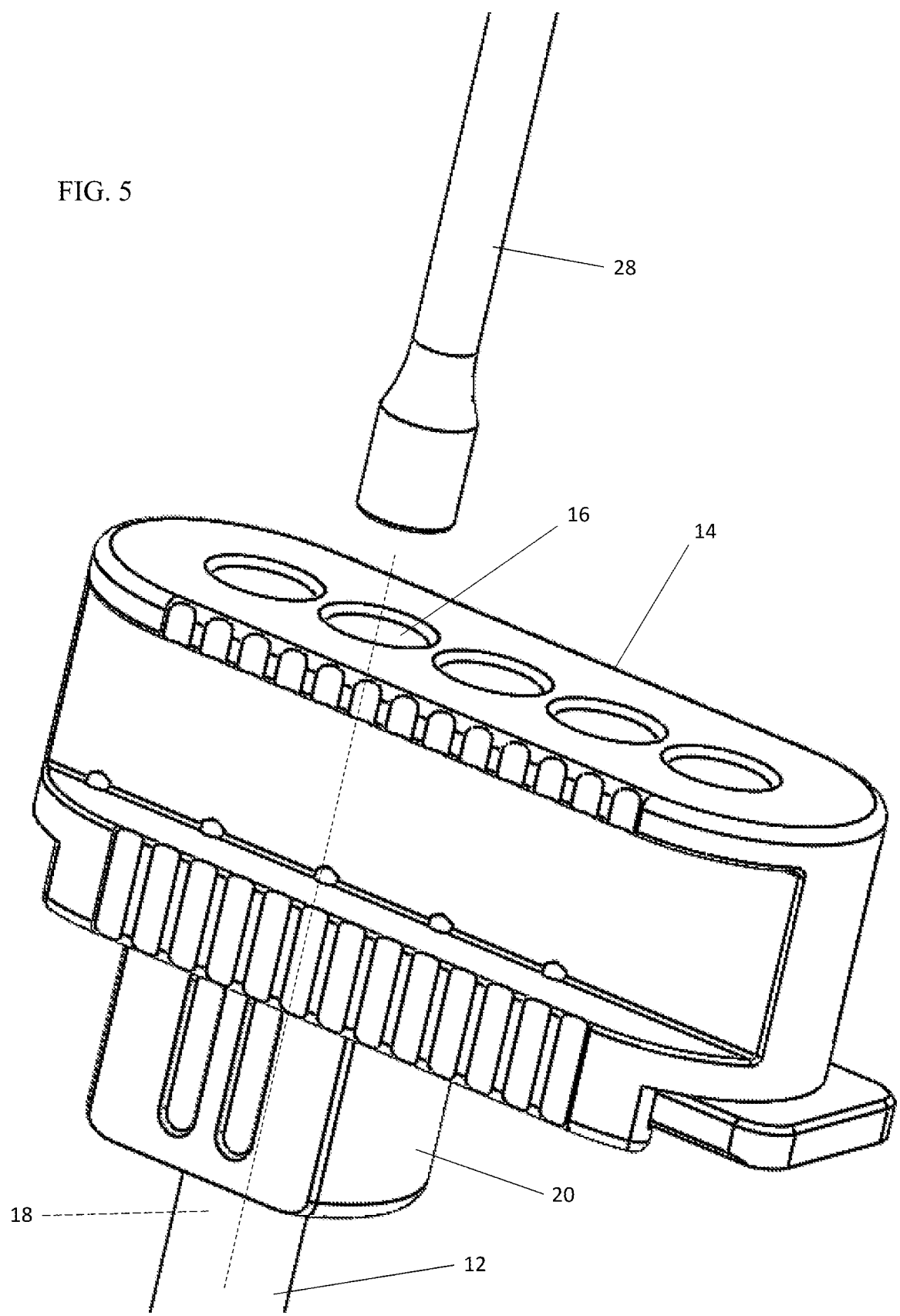
Figure 6:
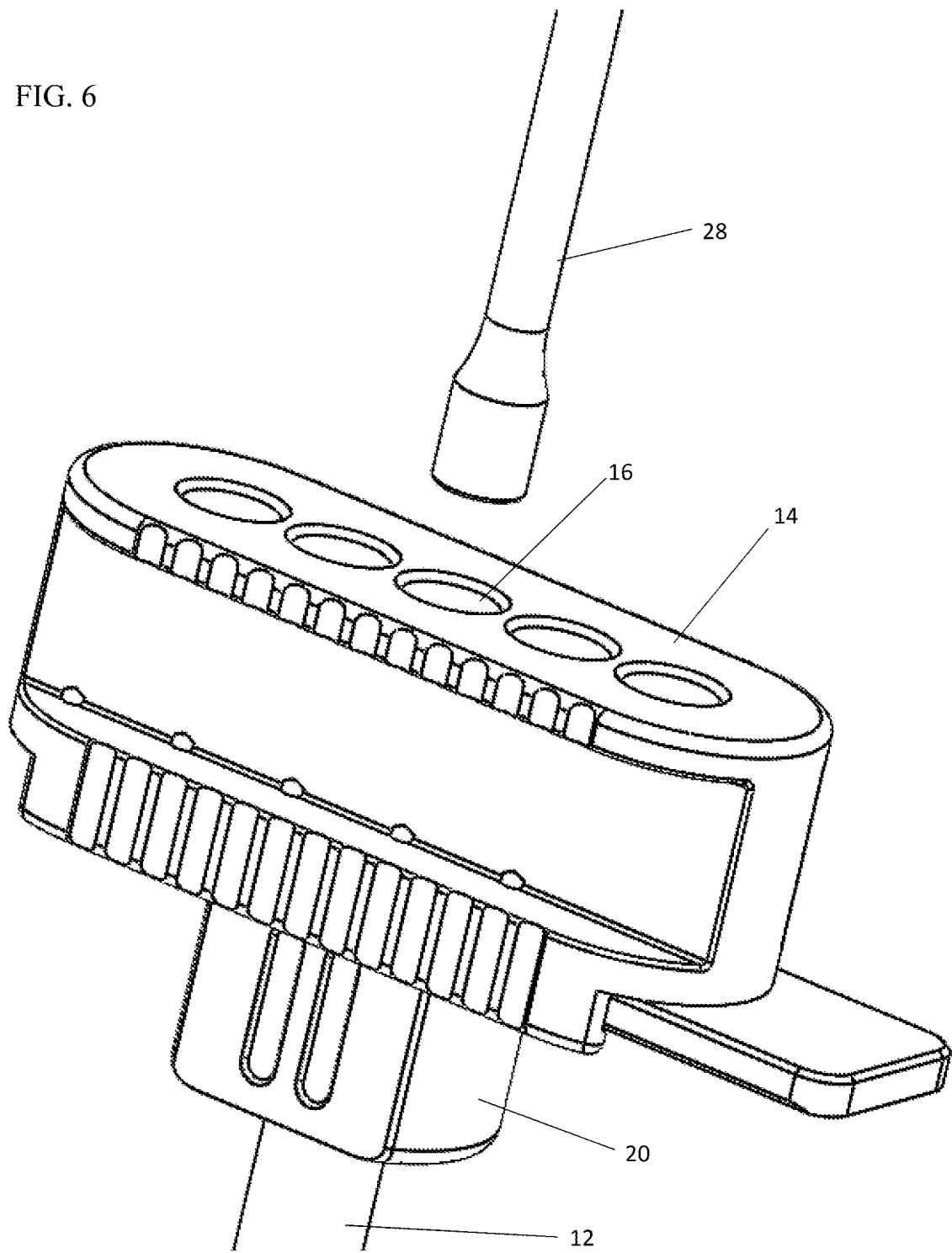
Figure 7:
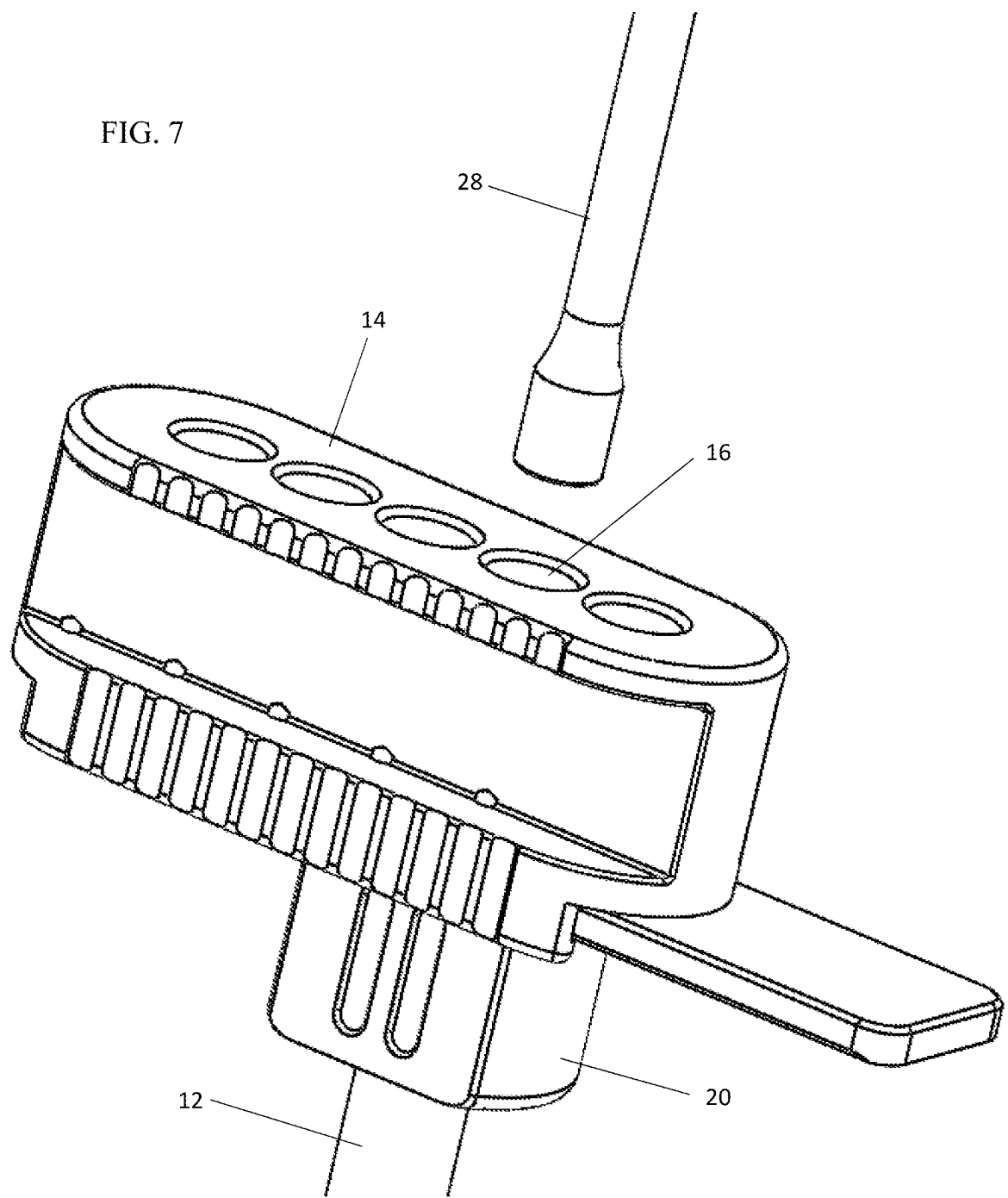
Figure 8:
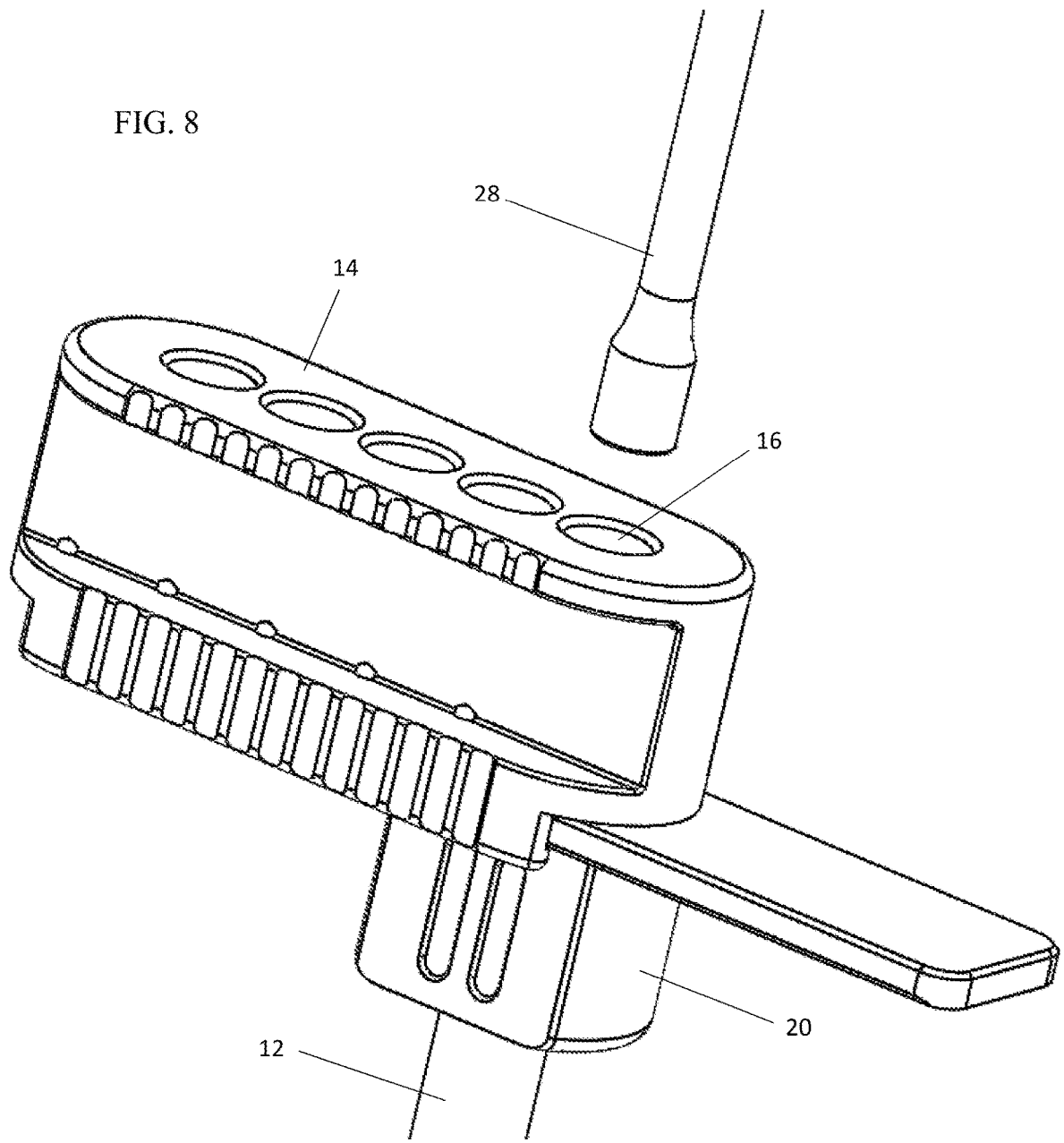

For use, as shown in FIG. 4, the block 14 is positioned relative to the channel 12 so that a first of the chambers 16 is in alignment with the lumen 18. As shown in dashed lines in FIGS. 4 and 5, a plunger 28 is introduced which is inserted into the chamber 16 and caused to be urged distally so as to push the graft material out of the chamber 16, through the lumen 18, and discharged in or about the interbody fusion device. The surgeon may adjust the block 14 as needed to utilize a sufficient number of the chambers 16 to permit a desired amount of graft material to be discharged in or about the interbody fusion device. As shown between FIGS. 4-8, the block 14 may be adjusted in series to allow for the sequential discharging of the chambers 16 utilizing the plunger 28. Once it is determined that sufficient graft material has been located in and about the interbody fusion device, the system 10 is removed from the interbody fusion device.

Figure 11:
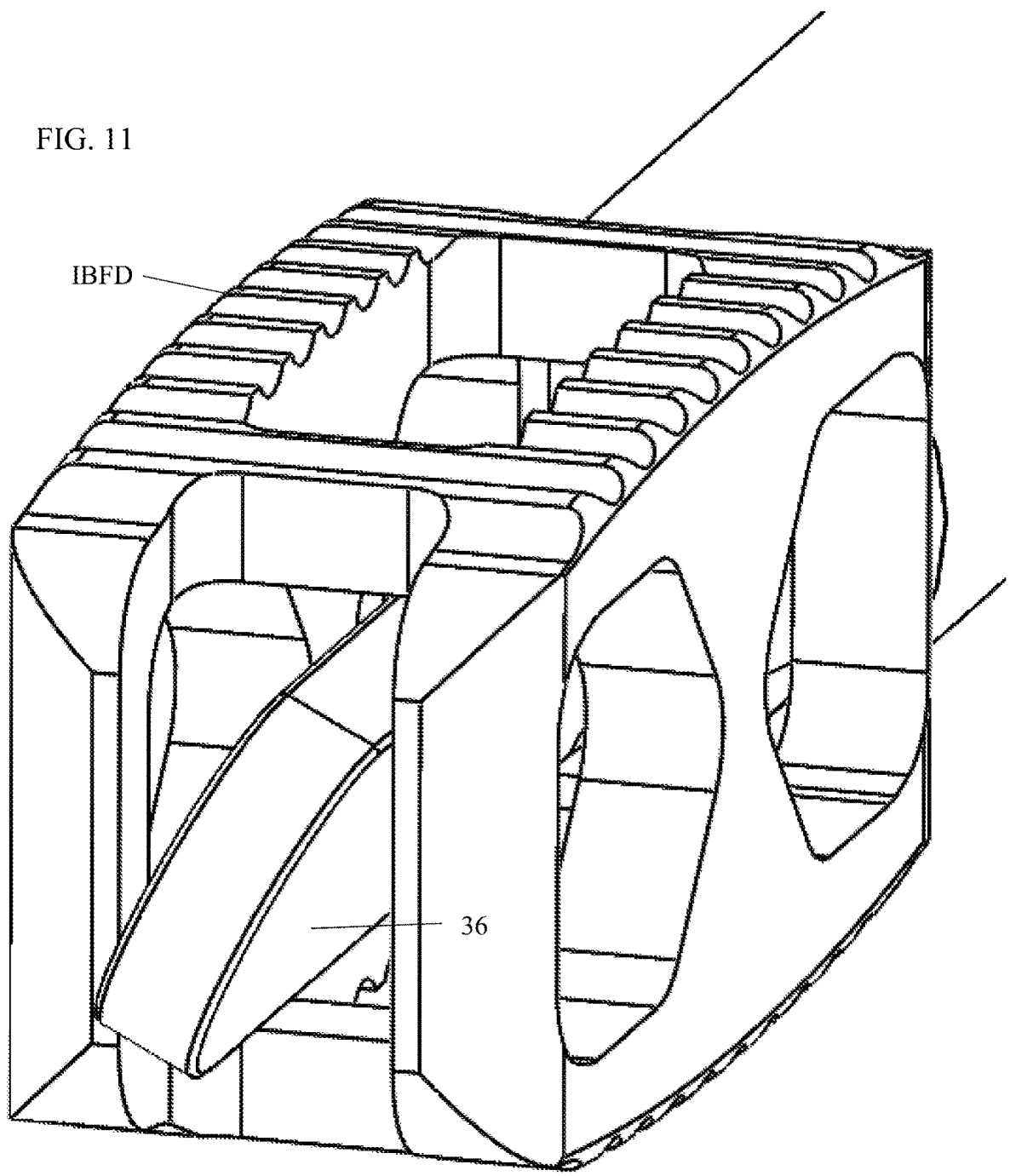
FIGS. 11 and 12 are enlarged perspective views showing the tamper paddles of FIGS. 9 and 10 in rotated dispositions within the interior of the interbody fusion device.
Figure 12:
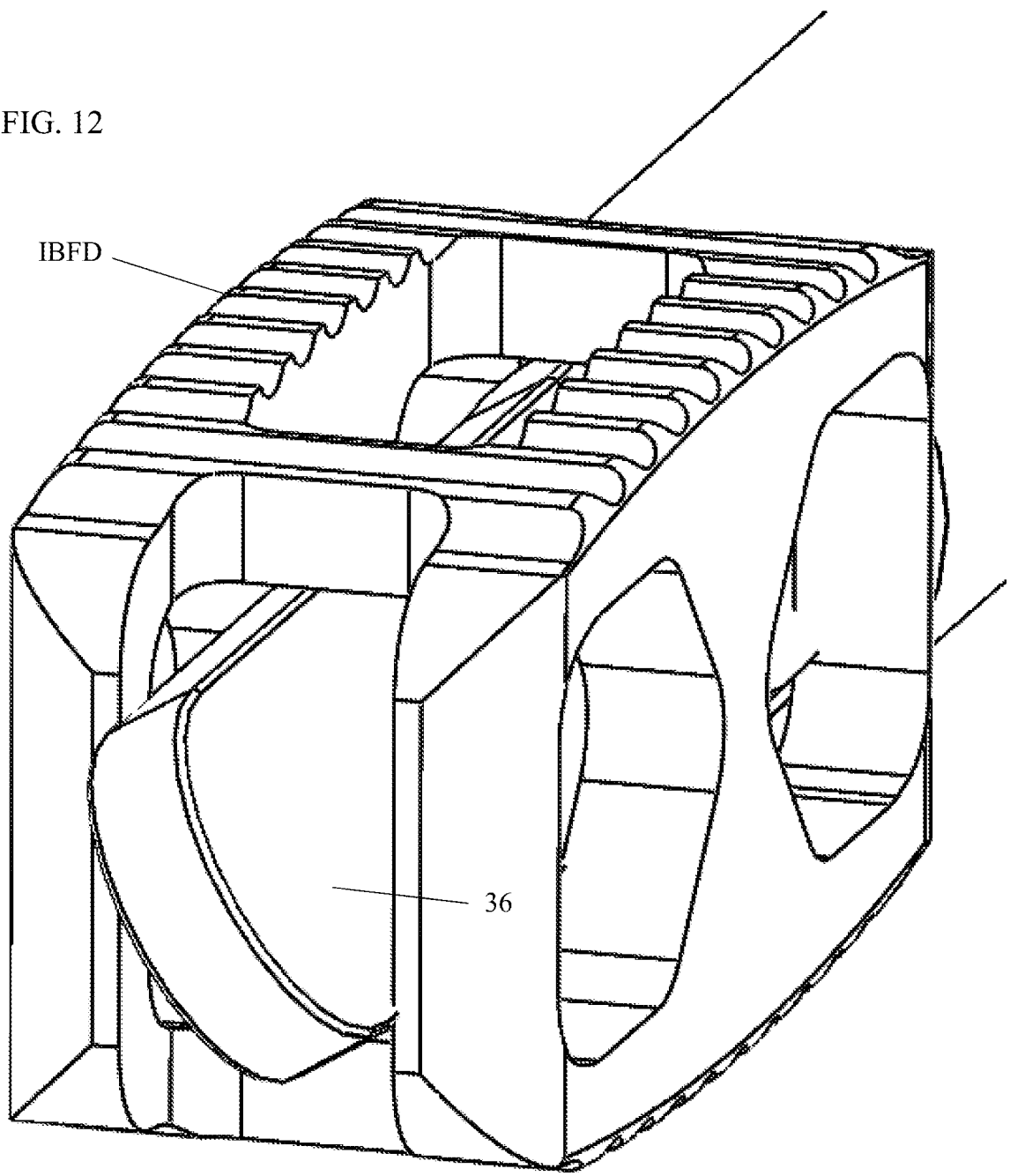
Figure 13:
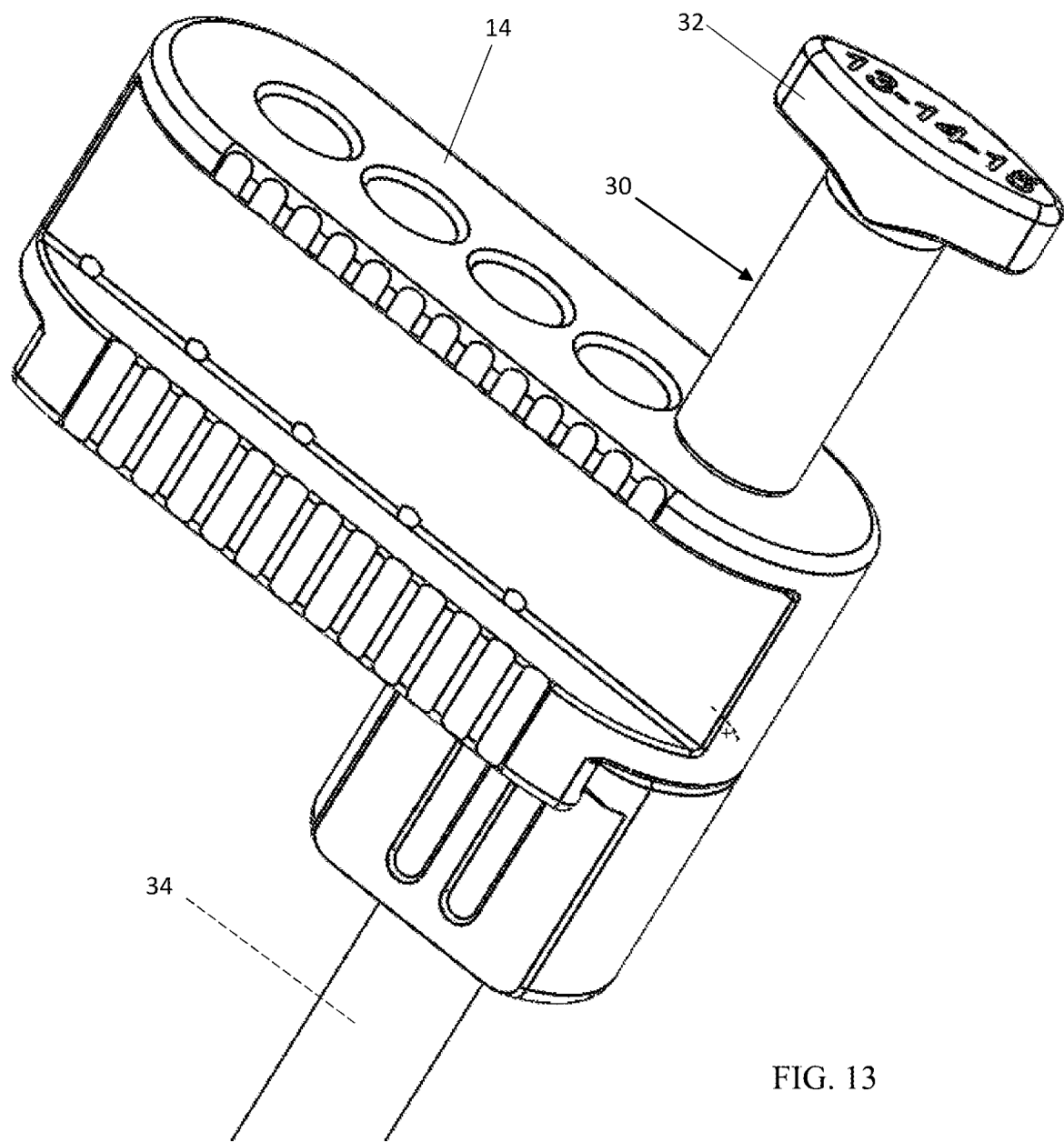
FIGS. 13 and 14 are enlarged perspective views showing the rotation of the tamper handles corresponding respectively with the rotation of the tamper paddles of FIGS. 11 and 12.
Figure 14:
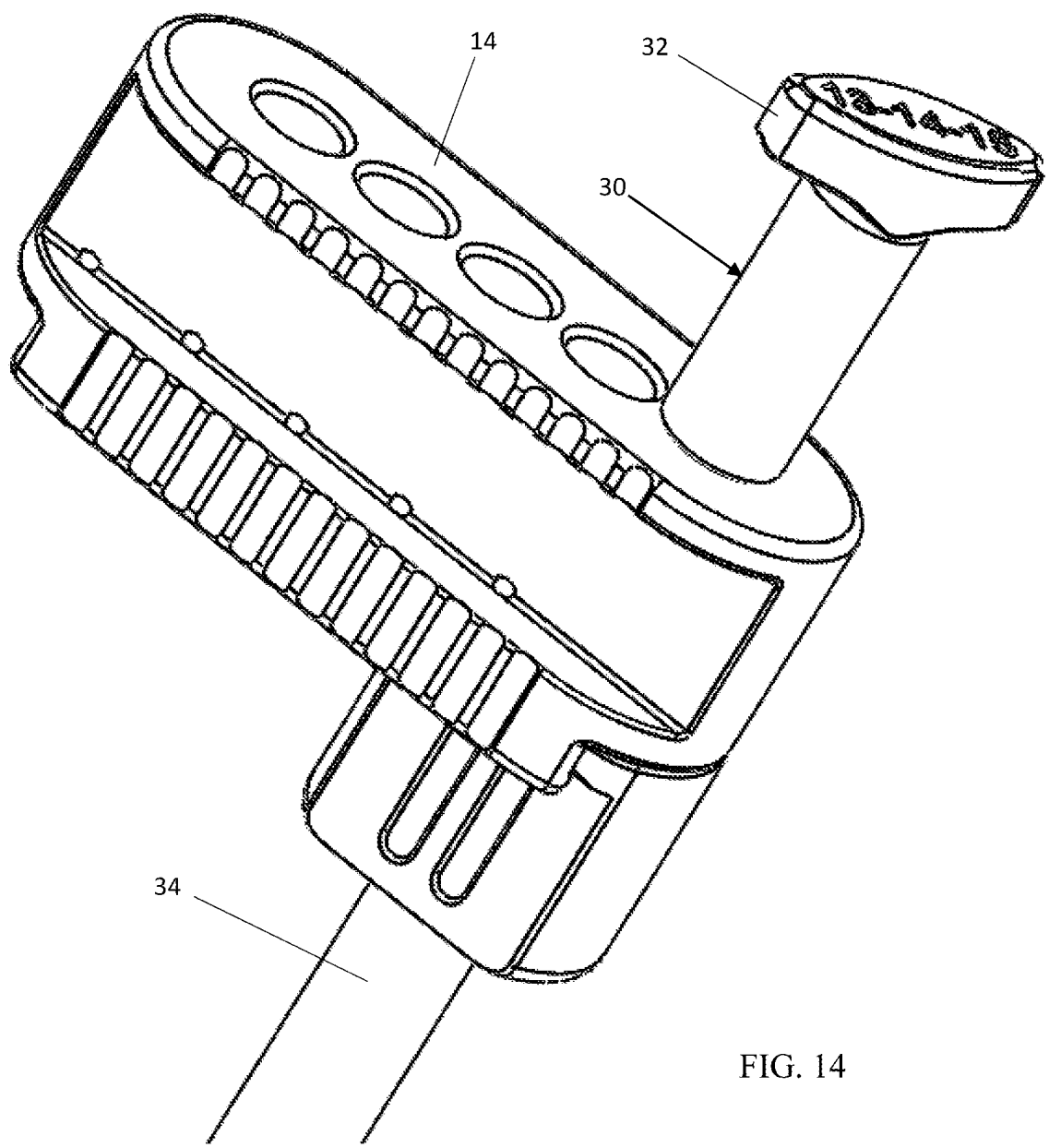

Optionally, as shown in FIGS. 9-14, one or more tampers 30 may be provided for tamping the graft material that has been discharged into and about the interbody fusion device. Each of the tampers 30 includes a handle 32 from which extends rod 34 with a paddle 36 at a distal end thereof. The tampers 30 are formed to extend through one of the chambers 16 and the lumen 18, past the distal end of the channel 12. The handle 32 may be formed to act as a stop in limiting the depth of insertion of the tamper 30 into the chamber 16. The paddle 36 is preferably formed to be inserted into an interior of an interbody fusion device. A distal end 38 of the paddle 36 may be formed atraumatic, such as having rounded corners. With introduction of the paddle 36 into the interbody fusion device, as shown in FIGS. 13 and 14, the handle 32 may be rotated resulting in corresponding rotation of the paddle 36 (FIGS. 11 and 12). In this manner, graft material may be tamped to better fill in voids in the intradiscal space, inside and about the interbody fusion device. A set of the tampers 30 may be provided with the system 10 having differently dimensioned paddles 36 to allow for different levels of tamping. The tampers 30 may be used at any point during introduction of the graft material.

The chambers 16 may be partially filled with the graft material in preparation for being implanted. This may allow for a more complete delivery of a dose of graft material from the respective chamber 16. With a smaller dose, a more complete urging of the material may be achievable, along with a more thorough tamping. This will depend on characteristics of the graft material.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. An interbody fusion system comprising an interbody fusion device for implantation into an intradiscal space of a spine, and an apparatus for delivering bone graft material into said interbody fusion device, wherein said interbody fusion device comprises:
   a distal end and a proximal end, opposing spaced side walls and opposing top and bottom surfaces defining an open-frame architecture with a hollow interior and an opening through each of said sidewalls, said top and bottom surfaces and at least through its proximal end, each opening being in communication with said hollow interior, and
   wherein said apparatus for delivering bone graft material comprises:
   an elongate channel having a distal end and a proximal end and a lumen extending therethrough, said distal end including an engagement feature for engaging the proximal end of said interbody fusion device in a manner to align said lumen of said channel with said opening through the proximal end of said interbody fusion device, and an adjustable block detachably and movably supported by said elongate channel, said block containing a plurality of spaced openings individually sequentially alignable with said lumen, each opening containing an individual graft pellet, said block being supported by said elongate channel for transverse movement relative to said elongate channel to align each of said respective block openings individually with said lumen of said elongate channel for delivery of each graft pellet individually into said hollow interior of said interbody fusion device.

2. The interbody fusion system of claim 1, wherein a releasable locking mechanism is provided between said elongate channel and said adjustable block to maintain each of said block openings in a surmountable aligned position relative to said lumen.

3. The interbody system of claim 2, wherein said releasable locking mechanism comprises a resilient and surmountable arrangement that provides resistance associated with each block opening and that requires a threshold amount of manual force to overcome said resistance to incrementally move said adjustable block relative to said channel.

4. The interbody fusion system of claim 3, wherein said resilient and surmountable arrangement comprises a plurality of locking apertures formed in said adjustable block.

5. The interbody fusion system of claim 4, wherein said resilient and surmountable arrangement comprises a releasable locking member seatable in one of a plurality of locking apertures each of which is associated with one of said block openings.

6. The interbody fusion system of claim 1, wherein said interbody fusion device is configured to be expandable.

7. The interbody fusion system of claim 1, wherein said interbody fusion device is configured of fixed height.

8. The interbody system of claim 1, further comprising a paddle configured to extend through one of said block openings and said channel lumen, said paddle having a length to be inserted past the distal end of said channel and into said interior of said interbody fusion device.

\* \* \* \* \*